(12) United States Patent
Becker et al.

(10) Patent No.: US 7,450,688 B2
(45) Date of Patent: Nov. 11, 2008

(54) LOW SKIN DOSE PATIENT POSITIONING DEVICE FOR RADIATION TREATMENT OF PRONE BREAST

(75) Inventors: Stewart John Becker, New York, NY (US); Thomas Rockwell Mackie, Verona, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 192 days.

(21) Appl. No.: 11/490,617

(22) Filed: Jul. 21, 2006

(65) Prior Publication Data
US 2007/0036267 A1    Feb. 15, 2007

Related U.S. Application Data

(60) Provisional application No. 60/701,922, filed on Jul. 22, 2005.

(51) Int. Cl.
*H05G 1/00*    (2006.01)

(52) U.S. Cl. .............................. 378/68; 378/37; 378/208
(58) Field of Classification Search ................... 378/37, 378/195–196, 208–209, 64–65, 68
See application file for complete search history.

(56) References Cited

U.S. PATENT DOCUMENTS

| 5,971,998 | A  | * | 10/1999 | Russell et al. ................ 606/130 |
| 6,463,122 | B1 | * | 10/2002 | Moore .......................... 378/65 |
| 2007/0223652 | A1 | * | 9/2007 | Galkin ........................ 378/37 |

* cited by examiner

*Primary Examiner*—Hoon Song
(74) *Attorney, Agent, or Firm*—Boyle Fredrickson, S.C.

(57) ABSTRACT

The present invention provides a support for a patient undergoing radiation therapy that preserves radiation build-up, such as normally spares the skin from receiving high amounts of radiation dose. The support includes at least one gas-filled bladder that displaces some tissue from the path of the radiation and/or spaces the tissue being treated from foam or the like.

14 Claims, 3 Drawing Sheets

LOW SKIN DOSE PATIENT POSITIONING DEVICE FOR RADIATION TREATMENT OF PRONE BREAST

RELATED APPLICATIONS

This application claims the benefit of U.S. provisional filing 60/701,922, filed Jul. 22, 2005 hereby incorporated by reference.

FIELD OF THE INVENTION

The present invention relates to a patient positioning device for radiation therapy, and in particular, to a patient positioning device reducing skin radiation dose.

The treatment of breast cancer, for example, may include radiation therapy in which high-energy beams of radiation are focused on a tumor, or the region from which a tumor has been removed. For this purpose, it is desirable to extend the breast tissue away from the chest wall so as to reduce radiation exposure to the chest. This may be done conveniently by positioning the patient in a prone position on a table having an opening through which one breast may be pendent. U.S. Pat. No. 5,564,468, incorporated by reference, describes a commercially available table for this purpose.

Table systems of this type can be cumbersome to operate and install. Further, while the tabletop may be relatively thin, it may nevertheless block radiation directed at a breast laterally across the untreated breast.

BRIEF SUMMARY OF THE INVENTION

The present invention provides a patient positioning device that may rest on top of a table and which provides an opening for a pendant breast treatment of a prone patient. Importantly, a portion of the support in the path of radiation is a gas-filled bladder, to prevent premature build-up of the radiation that increases skin dose, and which may occur in other support materials such as cushioning foam. The result is a lightweight support eliminating table structure or the like that can block radiation, and further providing reduced skin dosage.

Specifically then, the present invention provides a patient positioning device for radiation treatment of a breast of a prone patient, the positioning device including an elevating support, positionable between a table surface and a torso of the prone patient to support the patient with a first breast positioned within an opening in the elevating support. The elevating support has a thickness sized to allow the first breast to descend pendent from the patient into the opening. At least a portion of the elevating support beneath the second breast of the patient is a gas-filled bladder compressing the second breast upward toward the patient.

Thus, it is an object of at least one embodiment of the invention to provide a simple and light-weight patient positioner that may be easily set up and removed from a table of a radiation therapy machine. The gas-filled bladder provides supporting structure that integrates with cushioning foam surrounding the bladder, eliminating the need for rigid cantilevered table elements or the like.

It is another object of at least one embodiment of the invention to provide a compliant and lightweight support structure that does not increase skin dose. The gas filled bladder provides support without interposing significant mass into the radiation beam.

The bladder may be filled with air.

It is thus another object of at least one embodiment of the invention to provide a simple, safe, and readily available gas for the bladder.

Alternatively, the bladder may be filled with helium.

It is thus another object of at least one embodiment of the invention to provide an extremely low-density gas that substantially decreases radiation build-up.

Portions of the elevating support inferior and superior to the opening may also be gas filled bladders.

Thus, it is another object of at least one embodiment of the invention to provide a support surface that provides extremely wide range of access angles for radiation of a prone breast and/or that reduces the build-up of radiation that has previously passed through another material.

The opening may be a notch in the elevating support, open to a side of the elevating support.

Thus, it is an object of at least one embodiment of the invention to provide at least one access angle that is wholly free from intervening support structure.

The elevating support may be substantially symmetric about a horizontal plane so that the first breast may be either the right or left breast and the support surface may accommodate the patient by flipping the support about a horizontal, lateral axis.

Thus, it is an object of at least one embodiment of the invention to provide a support surface that may be used for treatment of either breast without complex adjustment or the like.

The support surface may support the patient in a substantially level attitude above the tabletop.

Thus, it is an object of at least one embodiment of the invention to provide a comfortable attitude for the patient that does not increase pressure on one side of the patient.

The foregoing objects and advantages may not apply to all embodiments of the inventions and are not intended to define the scope of the invention, for which purpose claims are provided. In the following description, reference is made to the accompanying drawings, which form a part hereof, and in which there is shown by way of illustration, a preferred embodiment of the invention. Such embodiment also does not define the scope of the invention and reference must be made therefore to the claims for this purpose.

DETAILED DESCRIPTION OF THE PREFERRED EMBODIMENT

Figure 1:
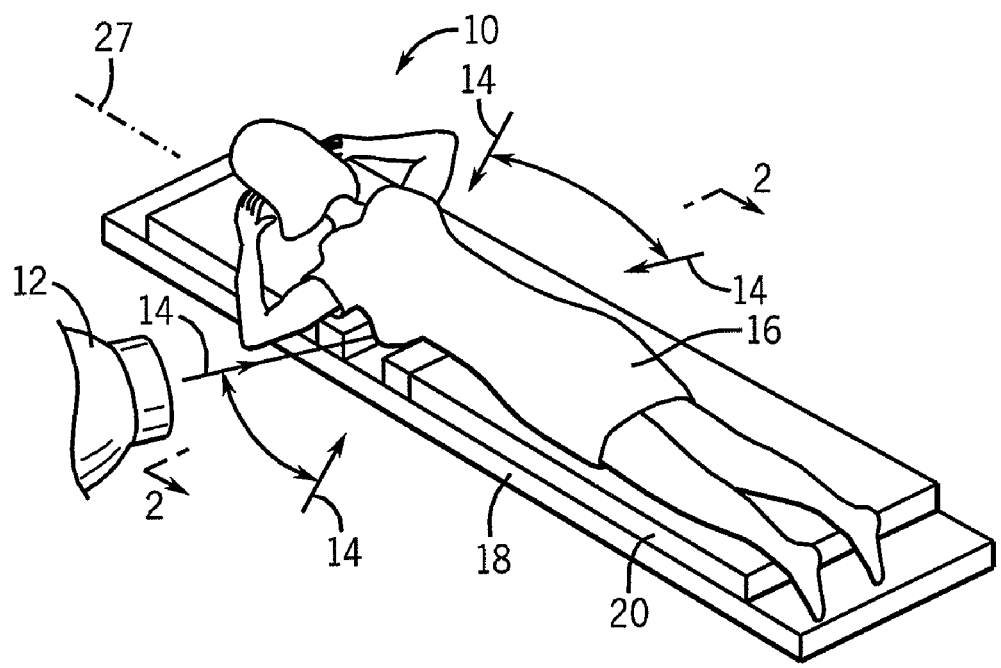
FIG. 1 is a perspective view of the support of the present invention as positioned on a treatment table and supporting a prone patient.

Referring now to FIG. 1, a radiation therapy machine 10 may include a radiation source 12 for directing a radiation beam 14 toward a patient 16 supported on a patient table 18 through a range of angles from two sides of the patient 16.

The present invention provides a patient positioning device 20 that may fit against the upper surface of the patient table 18 so that the patient 16 may lie prone on the upper surface of the patient positioning device 20 for radiation treatment of the breast.

Figure 2:
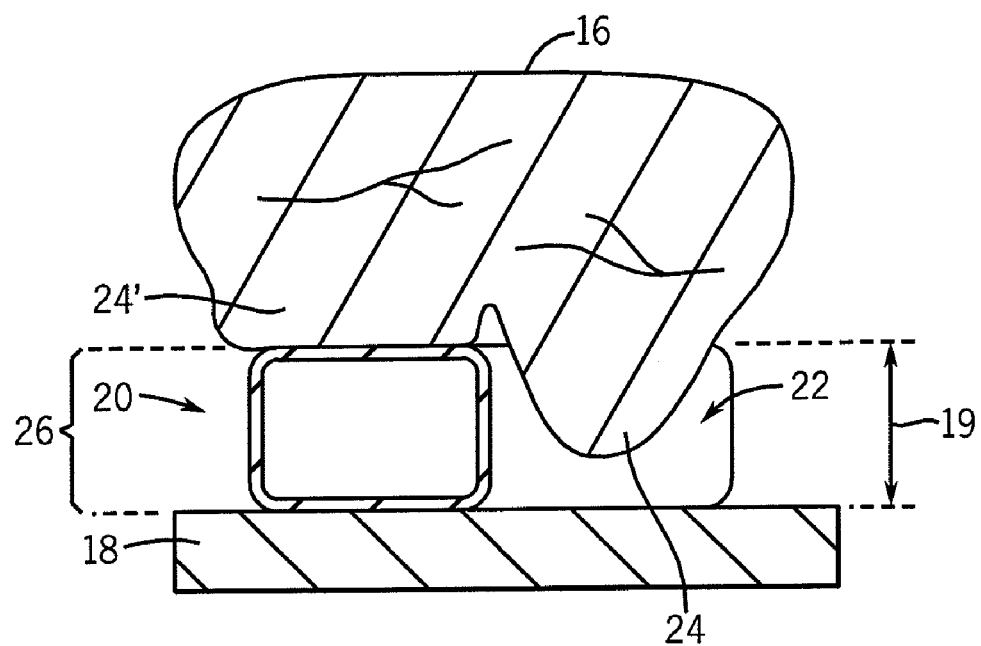
FIG. 2 is a cross-section through the support and patient of FIG. 1 along line 2-2, showing compression of a right breast upward out of the path of radiation and the pendent extension of the left breast using the present invention.

Referring now to FIG. 2, the patient positioning device 20 provides an opening 22 allowing one breast 24 of the patient 16 to extend pendent into the opening 22, drawn by the force of gravity downward toward the table 18. A thickness 19 of the patient positioning device 20 is such as to allow breast 24 to extend downwardly without interference with the table 18.

The remaining breast 24' is compressed upward towards the patient 16 by a portion of the patient positioning device 20, adjacent to the opening 22. In this way, only breast 24 extends into a generally horizontal treatment window 26, along which radiation beams 14 may pass, while breast 24' is compressed away from the treatment window 26.

Figure 3:
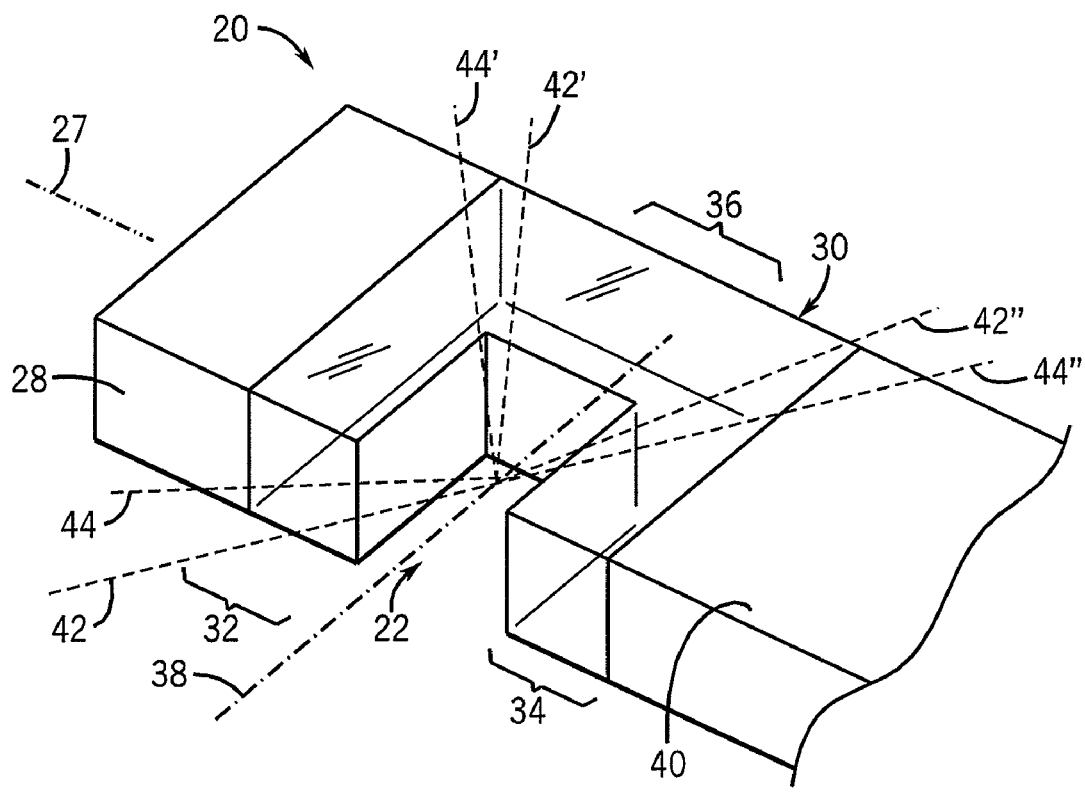
FIG. 3 is a fragmentary perspective detail of a first embodiment of the present invention, showing a "C" shaped gas bladder flanked by inferior and superior foam slabs.

Referring now to FIG. 3, the patient positioning device 20 preferably provides a cushion, extending generally along a longitudinal axis 27, aligned with the superior/inferior axis of the patient 16 when the patient 16 is positioned prone on the patient positioning device 20. A first elastomeric foam block 28, for example, being a closed-cell polyurethane foam, covered with a washable surface, may provide support for the patient's head and neck. Attached to an inferior side of foam block 28 is a "C" shaped gas bladder 30, defining the opening 22 with a parallelepiped upper leg 32 attached to the foam block 28, spaced from a parallelepiped lower leg 34 in parallel orientation as separated by spacer portion 36, extending approximately halfway across the width of the patient positioning device 20 along a lateral axis 38. The opening 22 is thus generally rectangular such as simplifies construction and surrounded on three sides by the parallelepiped upper leg 32 (on a superior side of the opening 22), the parallelepiped lower leg 34 (on an inferior side of the opening 22) and the spacer portion 36 (on a medial side of the opening 22). The lateral side of the opening 22 is unobstructed to provide free passage by the radiation beams 14.

Generally the width of the parallelepiped upper leg 32 and parallelepiped lower leg 34 along the longitudinal axis 27 will be at least three centimeters, to provide some decrease in lost build-up when radiation passes through the foam blocks 28 and 40 as will be described below An inferior side of leg 34 attaches to a second foam block 40, which provides support for the lower chest, pelvis, and upper legs of the patient 16. Foam blocks 28 and 40 and the "C" shaped gas bladder 30 all have the same thickness 19 near the "C" shaped gas bladder 30, but may taper away from the "C" shaped gas bladder 30.

When high-energy radiation beams 14 strike the skin, the dose of radiation deposited in the tissue gradually builds-up with depth so that the skin dose is relatively low and a higher dose is yielded beneath the skin, thus preventing painful and undesired radiation burns to the skin. The delay between the entry of the radiation into tissue and its point of maximum dose is called the build-up region and is desirably preserved for treatment of tumors beneath the skin. The present inventors have determined that a foam-filled nylon cushions can measurably exhaust the build-up distance, increasing the skin dose by as much as 300 percent when the breast is placed directly against the foam in comparison to the breast being placed directly against a gas-filled bladder. Accordingly, use of a bladder presents undesired loss of this build-up region and better control of the desired dose.

The "C" shaped gas bladder 30 is preferably constructed of a thin elastic material that provides a cushioning comparable to the cushioning provided by the foam blocks 28 and 40 to support the patient in generally horizontal attitude above the table 18. The "C" shaped gas bladder 30, for example, may be heat-sealed Mylar, vinyl, or other suitable material that can retain a gas under small amounts of pressure necessary to provide suitable cushioning. The bladder may be filled with air, or in a preferred embodiment, with helium, the latter having extremely low density and thus preserving radiation build-up length after the radiation strikes the breast 24. Internal gussets or battens (not shown) can be used to control the shape of the bladder 30

Figure 5:
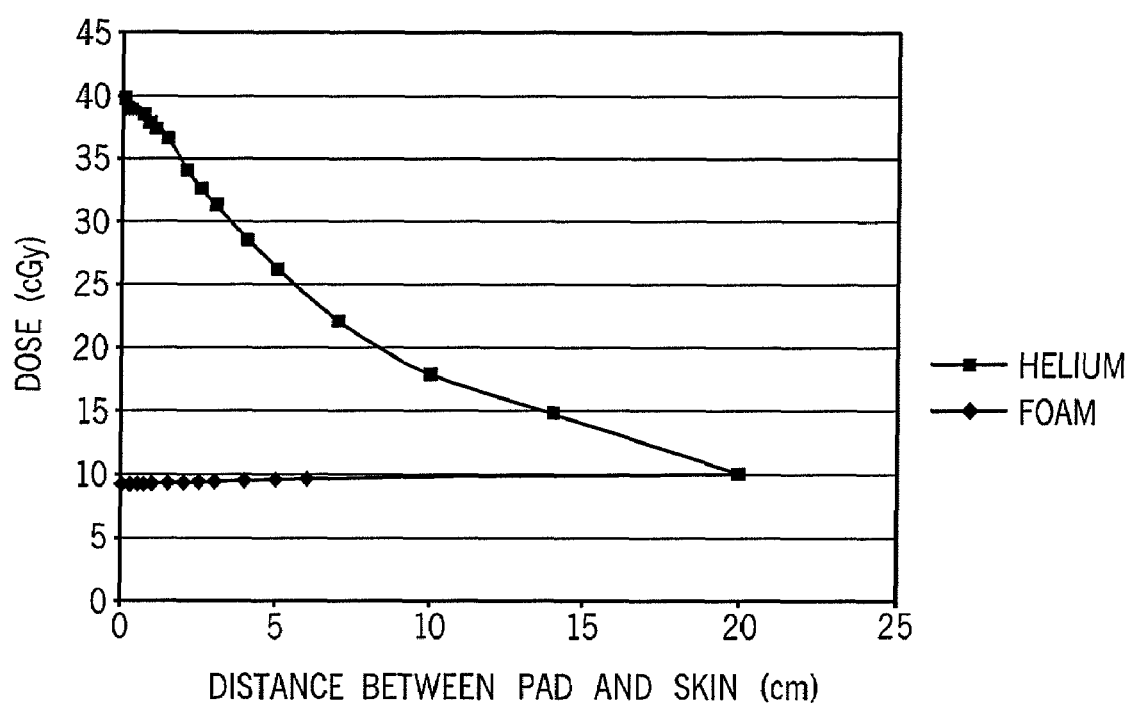
FIG. 5 is a chart showing the relative dose of radiation for one embodiment of the present invention as compared to a standard a foam pad at various distances from each, demonstrating the reduced build up of the present invention and the ability of the present invention to correct for some premature build-up when radiation passes through foam.

Referring momentarily to FIG. 5, on average, the skin will receive three to four times more dose when radiation passes through a foam pad touching the skin than when radiation passes through gas-filled bladder 30. As also shown in FIG. 5, the exhaustion of the build-up distance when radiation passes through foam is strongly dependent upon the distance between the foam and the breast and thus some passage through foam may be tolerated so long as the breast is spaced away from the foam, for example, by a gas filled bladder. Thus, the embodiment of FIG. 3 allows not only radiation directed along the lateral axis 38 (from either left or right sides of the patient 16), but along angled axis 42 (or 42') that pass through the upper leg 32 (from either left or right sides of the patient 16) or a similar axis 42" passing though only lower legs 34 from both sides of the patient 16, the left and right (only the patient right shown), but also through an angled axes 44 44' and 44" passing to some extent through portions of the foam block 28, where the loss of build-up is remedied by the spacing of the foam block 28 from the breast by the gas filled upper leg 32.

Figure 4:
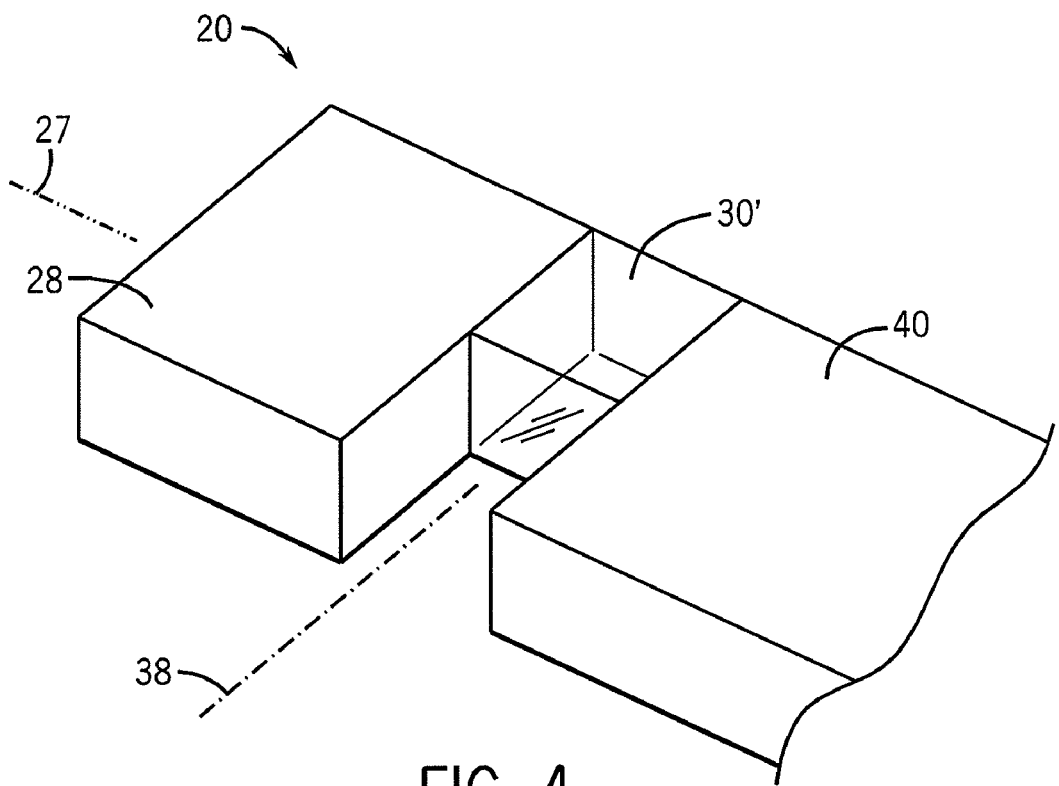
FIG. 4 is a figure similar to that of FIG. 3 showing an alternative embodiment with a single block-shaped gas bladder separating the superior and inferior foam slabs.

Referring now to FIG. 4, a simpler version of the present invention employs the foam blocks 28 and 40, separated from each other (to provide for the opening 22) by a generally parallelepiped gas bladder 30', that eliminates the complexity of the legs 32 and 34.

The bladders 30', and 30 described above, provides a spacing without eliminating the support of the patient which holds other tissue, including the opposed breast 24', away from the treatment window 26.

Referring to FIGS. 3 and 4, the patient support device 20 is generally symmetric about a horizontal axis (as used) and so may be flipped about the lateral axis 38 for use with either the left or right breast.

It will be understood that the invention need not be limited to radiation treatment of the breast, but may be used in any situation where radiation must pass through a cushioned support material into the patient and it is desired to reduce skin dosage. Further, the gas filled bladders may conform to the breast or other tissue to provide for stabilization.

It is specifically intended that the present invention not be limited to the embodiments and illustrations contained herein, but that modified forms of those embodiments including portions of the embodiments and combinations of elements of different embodiments also be included as come within the scope of the following claims.

We claim:

1. A patient positioning device for radiation treatment of a breast of a prone patient, the support comprising:
    an elevating support positionable between a table surface and a torso of the prone patient to support the patient with a first breast positioned within an opening in the elevating support,
    wherein the elevating support has a thickness sized to allow the first breast to descend pendant from the patient into the opening;
    wherein at least a portion of the elevating support beneath a second breast of the patient to compress the second breast upward toward the patient is a gas-filled bladder;
    whereby radiation is directed through the gas-filled bladder toward the first breast with reduced skin dose.

2. The patient positioning device of claim 1 wherein the bladder is filled with air.

3. The patient positioning device of claim 1 wherein the bladder is filled with helium.

4. The patient positioning device of claim 1 whereby further portions of the elevating support inferior and superior to the opening are gas filled bladders.

5. The patient positioning device of claim 1 wherein portions of the elevating support other than the gas-filled bladder are resilient foam.

6. The patient positioning device of claim 1 wherein the opening is a notch in the elevating support open to a side of the elevating support.

7. The patient positioning device of claim 1 wherein the elevating support is substantially symmetric about a horizontal plane so that the first breast may be either a left or right breast and the support surface may accommodate the patient in either case by flipping the support surface about a horizontal axis.

8. The patient positioning device of claim 1 wherein the elevating support positions the patient in a substantially level attitude.

9. A radiation therapy system comprising
    a radiation source directing radiation along an axis;
    a first patient positioning device intercepting the radiation along the axis before the radiation is received by the patient; and
    a second patient positioning device separating the first patient positioning device from the patient;
    wherein the second patient positioning device is a gas filled bladder sized to correct loss of build up caused by passage of the radiation through the first patient positioning device;
    whereby skin dose is reduced.

10. The radiation therapy system of claim 9 wherein the bladder is filled with air.

11. The radiation therapy system of claim 9 wherein the bladder is filled with helium.

12. The radiation therapy system of claim 9 wherein the first patient positioning device is a resilient foam.

13. The radiation therapy system of claim 9 wherein the second patient positioning device extends at least 3 cm along the radiation axis.

14. A method of providing radiation treatment of a breast comprising the steps of:
    (a) supporting a patient in prone position on an elevating support having an opening allowing the breast to extend pendant into the opening,
    (b) directing radiation along an axis passing through a portion of the elevating support before the radiation is received by the patient; and
    (c) wherein the portion is a gas filled bladder.

* * * * *